(12) United States Patent
Waldschläger et al.

(10) Patent No.: US 10,908,103 B2
(45) Date of Patent: Feb. 2, 2021

(54) X-RAY FLUORESCENCE SPECTROMETER

(71) Applicant: Bruker Nano GmbH, Berlin (DE)

(72) Inventors: Ulrich Waldschläger, Berlin (DE); Roald Alberto Tagle Berdan, Berlin (DE)

(73) Assignee: BRUKER NANO GMBH, Berlin (DE)

( * ) Notice: Subject to any disclaimer, the term of this patent is extended or adjusted under 35 U.S.C. 154(b) by 94 days.

(21) Appl. No.: 16/182,437

(22) Filed: Nov. 6, 2018

(65) Prior Publication Data
US 2019/0137422 A1    May 9, 2019

(30) Foreign Application Priority Data

Nov. 6, 2017   (EP) ..................... 17200054

(51) Int. Cl.
 *G01N 23/223*   (2006.01)
 *G21K 1/04*   (2006.01)
 *G21K 1/06*   (2006.01)

(52) U.S. Cl.
 CPC ..... *G01N 23/223* (2013.01); *G01N 2223/076* (2013.01); *G01N 2223/204* (2013.01);
(Continued)

(58) Field of Classification Search
 CPC .. G01N 2223/076; G01N 23/223; G21K 1/04; G21K 1/043
 See application file for complete search history.

(56) References Cited

U.S. PATENT DOCUMENTS 5,604,353 A * 2/1997 Gibson .................... G21K 1/06
                                                         250/505.1
2001/0021242 A1   9/2001 Bjeoumikhov et al.
(Continued)

FOREIGN PATENT DOCUMENTS

| CN | 106 996 941 A | 8/2017 | |
| CN | 106996941 A * | 8/2017 | ........... G01N 23/223 |
| WO | WO 2016/023975 A1 | 2/2016 | |

OTHER PUBLICATIONS

Sun, Xuepeng et al.; "Combined optic system based on polycapillary X-ray optics and single-bounce monocapillary optics for focusing x-rays from a conventional laboratory X-ray source"; Nuclear Instruments and Methods in Physics Research; vol. 802; Dec. 2015; pp. 5-9.

(Continued)

*Primary Examiner* — Chih-Cheng Kao
(74) *Attorney, Agent, or Firm* — Lewis Roca Rothgerber Christie LLP

(57) ABSTRACT

The present invention relates to an X-ray fluorescence, XRF, spectrometer, for measuring X-ray fluorescence emitted by a target, wherein the XRF spectrometer comprises an X-ray tube with an anode to emit a divergent X-ray beam, a capillary lens that is configured to focus the divergent X-ray beam on the target, an aperture system that is positioned between the anode of the X-ray tube and the capillary lens and comprises at least one pinhole, and a detector that is configured for detecting X-ray fluorescence radiation emitted by the target, wherein the at least one pinhole is configured for being inserted into the divergent X-ray beam and for reducing a beam cross section of the divergent X-ray beam between the anode and the capillary lens. The present invention further relates to an aperture system for a spectrometer, to the use of an aperture system for adjusting the focal depth of a spectrometer and to a method for adjusting the focal depth of as spectrometer.

10 Claims, 5 Drawing Sheets
(2 of 5 Drawing Sheet(s) Filed in Color)

(52) U.S. Cl.
CPC ........... *G01N 2223/316* (2013.01); *G01N 2223/3301* (2013.01); *G01N 2223/6113* (2013.01); *G21K 1/04* (2013.01); *G21K 1/067* (2013.01)

(56) References Cited

U.S. PATENT DOCUMENTS

| | | | | |
|---|---|---|---|---|
| 2007/0140423 | A1* | 6/2007 | Foland | G01N 23/20 |
| | | | | 378/57 |
| 2008/0084967 | A1 | 4/2008 | Matsuo et al. | |
| 2013/0221243 | A1* | 8/2013 | Perkins | G21K 1/04 |
| | | | | 250/492.3 |
| 2013/0287169 | A1* | 10/2013 | Liesenfelt | G01N 23/203 |
| | | | | 378/57 |
| 2014/0138542 | A1* | 5/2014 | Inada | G01N 23/2206 |
| | | | | 250/310 |

OTHER PUBLICATIONS

Extended European Search Report for corresponding European Patent Application No. 17200054.9, dated Aug. 3, 2018; 11pp.
Carolyn A. MacDonald, "Focusing Polycapillary Optics and Their Applications" in X-Ray Optics and Instrumentation, vol. 2010; Article ID 867049.

* cited by examiner (A)

(B)

(A)

(B)

(C)

X-RAY FLUORESCENCE SPECTROMETER

CROSS-REFERENCE TO RELATED APPLICATION(S)

This application is based upon and claims the benefit of priority of European Patent Application No. 17200054.9, filed on Nov. 6, 2017, the entire contents of which are incorporated herein by reference.

FIELD OF THE INVENTION

The present invention relates to an X-ray fluorescence, XRF, spectrometer, preferably to a micro-XRF spectrometer with a polycapillary X-ray optic, and to an aperture system for such an XRF spectrometer. The present invention further relates to a method for setting the focal depth of an X-ray fluorescence spectrometer and to the use of an aperture system according to the invention for setting the focal depth of an XRF spectrometer.

TECHNOLOGICAL BACKGROUND

X-ray fluorescence spectrometry, XRF, is widely used in scientific and commercial applications for non-destructive investigation of the composition of materials. Therein a target to be investigated is exposed to an incident beam of short-wavelength X-rays in contrary to the incident electron beams in energy dispersive X-ray spectroscopy, EDX. In response to the incident beam the target emits element specific fluorescence radiation that can be used for analyzing the elemental composition of the target.

It is usually distinguished between different standard methods of XRF, namely between the total reflection X-ray fluorescence spectrometry (TXRF), the grazing-incidence X-ray fluorescence spectrometry (GIXRF) and the micro X-ray fluorescence spectrometry (micro-XRF micro-RFA or μ-RFA), wherein the latter can be also performed with a three dimensional excitation volume as a 3D-μ-RFA or 3D-μ-XRF by using polycapillary optical lenses. Wherein the apparatuses and methods according to the present invention may be applied to any known XRF method, they are particularly suited for micro X-ray fluorescence spectrometry.

A typical XRF setup comprises an X-ray source, the excited radiation of which may pass trough a variety of filters before being directed onto a sample by a suitable X-ray optic.

Depending on the application such X-ray optics may comprise one or more of a zone plate, a polycapillary optic and a compound refractive lens. Polycapillary lenses are particularly suitable for μ-XRF and usually consist of a plurality of small hollow glass tubes that are arranged in an array and that each guide X-rays via a plurality of total external reflections.

A polycapillary lens images one X-ray point source to another. The polycapillary lens may thus be integrated in a XRF device via a goniometer or a similar device that allows for pivoting the optics in two or more spatial directions in order to raster a sample. An example of such scanning X-ray device utilizing a polycapillary lens is disclosed in WO 2016023975 A1.

The fluorescence radiation emitted by the sample may pass further filters before it is directed through a spectral analyzer for separation the distinct frequency components therein. The spectral analyzer might be upstream to or integrated into a detector that is configured to provide detector signals correspondingly to the intensity of the respective spectral components. As each of the emitted frequency signals corresponds to a certain element in the sample, the concentration of these elements can be determined based on these signals.

In order to allow for a sufficient X-ray intensity polycapillary lenses of rather high entrance aperture are utilized as X-ray optics in common spectrometers for a variety of XRF applications. Due to the imaging characteristics of polycapillary lenses these lenses also require rather large exit apertures for being able to focus the radiation on micrometer range spots. Consequently the exit aperture angles of the emitted radiation are also rather large and thus the usable focal depth of such spectrometers is rather low. This is particularly disadvantageous while performing radiometry on samples with higher topography, e.g. on printed circuit boards, PCBs, with a plurality of surface mounted devices of different height.

It is thus an object of the present invention to provide apparatuses and a method that allow for adjusting the focal depth of an X-ray fluorescence spectrometer as required for a certain application while still providing sufficient intensity for various XRF applications.

DESCRIPTION OF THE INVENTION

According to the present invention, the objective is solved and the disadvantages of the prior art are overcome or at least reduced by an X-ray fluorescence, XRF, spectrometer that is configured for measuring X-ray fluorescence emitted by a target in response to incident X-ray radiation. Therein, the XRF spectrometer of the invention comprises an X-ray tube with an anode that is configured for emitting a divergent X-ray beam. Preferably, in first approximation the anode resembles a point source. The XRF spectrometer further comprises a capillary lens, preferably a polycapillary lens, which is configured to focus the divergent X-ray beam on the target. Suitable focusing polycapillary lenses are known to the person skilled in the art and a review thereof can be found in the article: Carolyn A. MacDonald, "Focusing Polycapillary Optics and Their Applications" in *X-Ray Optics and Instrumentation*, vol. 2010, Article ID 867049, the whole content of which is incorporated herein by reference.

According to the present invention, the XRF spectrometer further comprises an aperture system that is positioned between the anode of the X-ray tube and the capillary lens, particularly between the anode of the X-ray tube and an entrance aperture of the capillary lens. The spectrometer further comprises a detector that is configured for detecting X-ray fluorescence radiation emitted by the target. Suitable detectors are known to the person skilled in the art. According to the present invention, the aperture system comprises at least one pinhole that is configured for being inserted into the divergent X-ray beam and for reducing a beam cross section of the divergent X-ray beam between the anode and the capillary lens. Preferably, the aperture system can be set to a first state, wherein the divergent X-ray beam between the anode and the polycapillary lens is unblocked, and a second state, wherein the divergent X-ray beam between the anode and the polycapillary lens is partially blocked. Therein, the cross section of the divergent X-ray beam is preferably reduced from the outer circumference of the divergent X-ray beam. Further preferred, the at least one pinhole is configured such that only inner parts of the divergent X-ray beam can pass the at least one pinhole. Preferably, the shape of the at least one pinhole is circular or rectangular, while other shapes of the pinhole, e.g. ring-shapes, can be utilized as well.

Within the XRF spectrometer of the present invention, specific characteristics of capillary, preferably polycapillary optics, are utilized for effectively adjusting the focal depth of the X-ray radiation used for exciting X-ray fluorescence within the target. Preferably, the capillary lens of the spectrometer of the invention essentially images a point source, e.g. a front focal point, on an image point, i.e. rear focal point, in a symmetric fashion. Therein, an entrance aperture and a front aperture angle of the capillary lens are essentially equal to its exit aperture and its rear aperture angle. Thus, by reducing the beam cross section of the primary X-ray radiation incident on the entrance aperture of the capillary lens, the beam width of the X-ray radiation exiting the capillary lens is also reduced. Hence, the focal depth, i.e. a length in which a focal size widens to a predetermined value before and behind a smallest focal spot, is increased.

Advantageously, by adjusting the beam cross section in front of the capillary lens, the focal depth at the illuminated target can be adjusted. The aperture system of the present invention therefore utilizes the restrictive imaging characteristics of capillary lenses. Thus, large parts of any scatter that may result from inserting the at least one pinhole of the aperture system in the divergent X-ray beam between anode and capillary lens are not imaged to the rear side of the capillary lens as the scattered radiation mostly does not satisfies the conditions for total external reflections within the capillaries of the capillary lens. Hence, the aperture system is advantageous over pinhole illumination on the rear side of the capillary lens. Further, the efficiency of light conduction is smaller in the outer parts of a capillary lens compared to the inner parts of the capillary lens. Thus, the gain in focal depth is advantageously not compensated by a loss of intensity. Further, the integration of the aperture system in the front of the capillary lens is easier than an integration in the rear of the polycapillary lens, e.g. due to the larger available construction space. The spectrometer of the present invention can be also advantageously used for energy dispersive X-ray spectroscopy. As described above the focal depth can be increased by reducing the beam divergence of the X-ray beam emitted by the capillary lens. Due to the narrower beam less Bragg reflexes are triggered in the sample and hence disturbing Bragg peaks in recorded spectrums are attenuated.

According to a preferred embodiment of the present invention, a front focal point of the capillary lens is placed at the anode of the X-ray tube of the spectrometer. By placing the source of the divergent X-ray beam at the front focal point of the capillary lens, advantageously all capillaries of the lens participate in the optical transmission of the X-rays. Further preferred, the X-ray tube is a microfocus tube, preferably providing a focal spot of primary X-ray radiation in the micrometer range at the anode of the tube. Suitable microfocus tubes are known to the person skilled in the art. Particularly preferred the focal spot of primary X-ray radiation at the anode has a beam size, i.e. diameter of the beam cross section, between 1 µm and 500 µm and further preferred between 5 µm and 30 µm. An XRF spectrometer comprising such microfocus tube preferably is a micro XRF spectrometer. The aperture system is disposed between the front focal point and the entrance aperture of the capillary lens and simulates a virtual source that may be considered to be positioned outside the focal point of the capillary lens.

Further preferred, the capillary lens has an entrance aperture, a front focal length, and a front aperture angle $\alpha$ that obey the equation $$\tan \alpha = \frac{\text{entrance aperture}}{\text{front focal length}}.$$

Therein, the entrance aperture corresponds to the diameter of area of the light receiving sides of the capillaries of the lens. The front focal length corresponds to the distance between the front focal point and the entrance aperture and the front aperture angle is the angle enclosed between an X-ray travelling from the front focal point to an outermost capillary of the lens and an optical axis of the lens. In the spectrometer according to the present invention, the front focal length preferably corresponds to the distance between the entrance aperture and the anode.

Preferably, the capillary lens further has an exit aperture, a rear focal length, and a rear aperture angle $\beta$ that obey the equation $$\tan \beta = \frac{\text{exit aperture}}{\text{rear focal length}}.$$

Therein, the exit aperture corresponds to the diameter of area of the light emitting sides of the capillaries of the lens. The rear focal length corresponds to the distance between the rear focal point and the exit aperture and the rear aperture angle is the angle enclosed between an X-ray travelling from an outermost capillary of the lens to the rear focal point and an optical axis of the lens. In this preferred embodiment, the rear focal length corresponds to the distance between the exit aperture and the target. In other words, the target is positioned in the rear focal point of the capillary lens.

According to a preferred embodiment, the aperture system and particularly the at least one pinhole of the aperture system is positioned at a minimum distance of 35 mm, further preferred of 30 mm and particularly preferred of 25 mm to the anode of the X-ray tube. Further preferred, the aperture system and particularly the at least one pinhole of the aperture system is positioned at a minimum distance to the capillary lens that corresponds to maximal 85%, further preferred maximal 90% and particularly preferred 95% of the focal front focal length of the capillary lens. Further preferred the aperture system and particularly the at least one pinhole of the aperture system is positioned at a position corresponding at least to 50%, further preferred to at least 60% and particularly preferred to at least 70% of the front focal length of the capillary lens. The reduction of the primary beams beam cross section is advantageously defined more precisely the closer the at least one pinhole is positioned at the entrance aperture of the capillary lens. Positioning the at least one pinhole closer to the anode of the X-ray tube disadvantageously increases edge blurring of the collimation at the entrance aperture due to the limited focus of the X-ray tube.

In a further preferred embodiment, the aperture system of the present invention comprises at least one pinhole of adjustable size. Principally one pinhole of adjustable size is sufficient for providing the functions of the at least one pinhole as described above, i.e. for adjusting the focal depth of the spectrometer. Particularly preferred the pinhole of adjustable size is formed by an iris diaphragm with adjustable diameter or by a rectangular aperture with adjustable size. Therein, the pinhole of adjustable size preferably comprises a first modification with a first size configured for letting pass the whole divergent X-ray beam and at least one second modification with a second size that is reduced for blocking a part of the divergent X-ray beam. In other words, the first size has a diameter of at least the beam width of the divergent X-ray beam at the position of the aperture system between the anode and the capillary lens.

According to another particularly preferred embodiment, the aperture system comprises a revolver comprising a plurality of pinholes with different sizes. Preferably the revolver is configured to insert each one of the pinholes into the divergent X-ray beam individually based on a rotational position of the revolver. Alternatively, the aperture system comprises a slider comprising a plurality of pinholes with different sizes. Preferably the slider is configured to insert each of the pinholes into the divergent X-ray beam individually based on a translational position of the slider. Therein, the plurality of pinholes comprises at least one first pinhole with a first size configured for letting pass the whole divergent x-ray beam and at least one second pinhole with a second size that is reduced for blocking a part of the divergent X-ray beam. Further preferred, the first pinhole has a size of at least the beam width of the divergent X-ray beam at the position of the aperture system between the anode and the capillary lens.

Further preferred, the revolver or slider of the above embodiment further comprises at least one filter, particularly preferred a filter foil, for spectrally modifying the divergent X-ray beam. Preferably, at least one spectral filter is disposed at the same translational position of the slider or the same rotational position of the revolver, respectively, as one of the plurality of pinholes. In other words, the functionality of setting the focal depth of the spectrometer is integrated with a further functionality of spectrally modifying the primary X-ray radiation. In such an embodiment, preferably each of a plurality of pinholes is combined with one of a plurality of identic filters.

According to an alternative embodiment of the spectrometer, at least one spectral filter is preferably disposed at a different translational position of the slider or at a different rotational position of the revolver, respectively, compared to each of the plurality of pinholes. In such an embodiment, the functionalities of spectral modification and adjustment of focal depth are provided separately by the aperture system. Such an embodiment might be used in a case that a spectral modification is solely required for an unaltered focal depth and intensity.

Further preferred, the XRF spectrometer of the invention, preferably comprising a revolver or slider with a plurality of pinholes of different sizes as described above, comprises an additional revolver or slider with at least one filter for spectrally modifying the divergent X-ray beam. Hence, functionalities regarding the spectral modification of the primary X-ray beam are integrated in the aperture system of the present invention as a separate functional unit.

According to a further preferred embodiment, the XRF spectrometer of the present invention comprises a movable target stage that is configured for receiving the target and for being moved in X- and Y-direction, preferably also in Z-direction. Various implementations for moving a target or sample stage in one or more directions are known to the skilled person, may comprise micro actuators, linear actuators, piezo actuators and/or goniometers. Further preferred, the movable target stage is configured as at least one of a tip, tilt and/or rotation stages, e.g. as a zeta/xi tilt stage. Additionally or alternatively, preferably the X-ray source and/or the capillary optic of the XRF spectrometer of the present invention are configured to be pivotable and/or movable. Particularly preferred, the capillary optic of the XRF spectrometer of the invention is mechanically connected to a goniometer mechanism that is configured for pivoting the capillary optic about at least one pivoting axis, as e.g. described in WO 2016/023975 A1, the full content of which is incorporated herein by reference. By providing the XRF spectrometer of the invention with a movable target stage, X-ray source and/or X-ray optic, a scanning, e.g. a line- or point-wise scanning of the target is enabled.

Further preferred, the XRF spectrometer of the present invention comprises a control unit that is configured for controlling the aperture system. Therein, the control unit is configured to adapt the focal depth of the XRF spectrometer. The control unit is preferably configured to insert one of the at least one pinhole into the primary X-ray beam between the anode of the X-ray source and the capillary lens. Therein, the control unit is further preferred to insert one of the at least one pinhole into the primary X-ray beam based on a topography of the sample. Therein, data on the topography of the sample may be provided to the control unit from a database or a user interface or may be acquired by the control unit by utilizing the XRF spectrometer for detecting topography of the sample. Therein, the topography of the sample refers to the roughness of the sample as well as to the overall geometry and shape of a three-dimensional sample. Further preferred, the control unit is configured for controlling at least one of the movable target stage, X-ray source and/or X-ray optic (capillary optic) for enabling scanning of the target. Further preferred, the control unit is configured for adapting the focal depth of the XRF spectrometer during scanning of the target. Therein, the focal depth may be adapted to local variations in topography of the target, e.g. of an oil painting or microelectronic components surface mounted to a PCB, or to global variations in topography of the target, e.g. to the shape of a three-dimensional object, particularly at its edges.

Another aspect of the present invention relates to an aperture system for an X-ray fluorescence spectrometer with an X-ray tube and a capillary lens. Therein, the aperture system of the present invention comprises at least one pinhole that is configured to be positioned between an anode of the X-ray tube and the capillary lens and is further configured for reducing a beam cross section of a divergent X-ray beam emitted by the anode. In other words, the aperture system of the invention comprises at least one pinhole with a size, e.g. a diameter, which is smaller than the size, e.g. the diameter, of the divergent X-ray beam of an XRF spectrometer at a destined installation position of the aperture system between the anode and the capillary lens of the spectrometer. Hence, the sizes of the at least one pinhole are adapted to the installation position of the aperture system within the spectrometer. By integrating the aperture system of the invention into an XRF spectrometer, particularly a μ-XRF spectrometer, comprising an X-ray tube with an anode and a capillary lens, at an installation position between the anode and the capillary lens, a focal depth of the spectrometer can be adjusted by varying the size of a pinhole inserted into the X-ray beam.

According to a preferred embodiment, the aperture system and particularly the at least one pinhole of the aperture system is configured to be positioned at a minimum distance of 35 mm, further preferred of 30 mm and particularly preferred of 25 mm to the anode of the X-ray tube. Further preferred, the aperture system and particularly the at least one pinhole of the aperture system is configured to be positioned at a minimum distance to the capillary lens that corresponds to maximal 85%, further preferred maximal 90% and particularly preferred 95% of the focal front focal length of the capillary lens. Further preferred the aperture system and particularly the at least one pinhole of the aperture system is configured to be positioned at a position corresponding at least to 50%, further preferred to at least 60% and particularly preferred to at least 70% of the front focal length of the capillary lens. The reduction of the primary beams beam cross section is advantageously defined more precisely the closer the at least one pinhole is positioned at the entrance aperture of the capillary lens. Positioning the at least one pinhole closer to the anode of the X-ray tube disadvantageously increases edge blurring of the collimation at the entrance aperture due to the limited focus of the X-ray tube.

Preferably, the aperture system has the features as described above with respect to an aperture system of a spectrometer according to the invention. Particularly preferred, the aperture system further comprises a revolver comprising a plurality of pinholes with different sizes. Preferably the revolver is configured to insert each one of the pinholes individually into the divergent X-ray beam based on a rotational position of the revolver. Alternatively, the aperture system comprises a slider comprising a plurality of pinholes with different sizes. Preferably the slider is configured to insert each one of the pinholes individually into the divergent X-ray beam based on a translational position of the slider. Therein, the plurality of pinholes comprises at least one first pinhole with a first size configured for letting pass the whole divergent X-ray beam and at least one second pinhole with a second size that is reduced for blocking a part of the divergent X-ray beam. In other words, the first pinhole has a size of at least the primary X-ray beam width and the second pinhole has a size lower than the primary X-ray beam width at the destined installation position of the aperture system.

Additionally or alternatively, the aperture system of the present invention comprises at least one pinhole of adjustable size. Therein, the one pinhole of adjustable size is preferably sufficient for providing the functions of the at least one pinhole as described above with respect to the spectrometer, i.e. for adjusting the focal depth of the spectrometer. Particularly preferred the pinhole of adjustable size is formed by an iris diaphragm with adjustable diameter or by a rectangular aperture with adjustable size. Therein, a the pinhole of adjustable preferably comprises a first modification with a first size configured for letting pass the whole divergent X-ray beam at the installation position of the aperture system and at least one second modification with a second size that is reduced for blocking a part of the divergent X-ray beam at the installation position of the aperture system. Preferably, the first size has a diameter of at least the beam width of the divergent X-ray beam at the installation position of the aperture system and the second size has a diameter smaller than the beam width of the divergent X-ray beam at the at the installation position of the aperture system.

According to a preferred embodiment, the revolver or slider of the aperture system further comprises at least one filter for spectrally modifying the divergent X-ray beam. Therein, at least one filter is preferably disposed at the same translational position of the slider or the same rotational position of the revolver, respectively, as one of the plurality of pinholes. In other words, the functions of setting the focal depth of the spectrometer is integrated with a further functionality of spectrally modifying the primary X-ray radiation. In such embodiment, preferably each of a plurality of pinholes is combined with one of a plurality of identic filters.

According to an alternative embodiment of the aperture system at least one spectral filter is disposed at a different translational position of the slider or at a different rotational position of the revolver, respectively, than one of the plurality of pinholes. In such an embodiment, the functionalities of spectral modification and of adjusting the focal depth are provided separately, e.g. in a case wherein spectral modification is solely required for unaltered focal depth and intensity. Further preferred, the XRF spectrometer of the invention, preferably comprising a revolver or slider with a plurality of pinholes of different sizes as described above, comprises an additional revolver or slider with at least one filter for spectrally modifying the divergent X-ray beam. Thus, the functionality of spectral modifying the primary X-ray beam is integrated in the aperture system of the present invention as a functional unit.

Another aspect of the present invention relates to a method for adjusting the focal depth $d_F$ of an X-ray fluorescence, XRF, spectrometer that comprises at least an X-ray tube with an anode emitting a divergent X-ray beam, a capillary lens configured to focus the divergent X-ray beam on a target, and an aperture system positioned between the anode and the capillary lens. Therein, the aperture system comprises at least one pinhole, preferably the aperture system is an aperture system according to the invention as described above. The method of the invention comprises the step of inserting one of the at least one pinhole in the divergent X-ray beam between the anode of the X-ray tube and the capillary lens.

Inserting a specific one of the at least one pinholes reduces the cross section of the divergent X-ray beam between the anode and the capillary lens. Hence, the section of the entrance aperture of the capillary lens that is illuminated by the primary X-ray radiation is reduced. Thus, the front aperture angle $\alpha$ of the capillary lens, i.e. the angle enclosed by an X-ray beam travelling from the anode to an outermost illuminated capillary of the lens and the optical axis of the lens is also reduced. Based on the symmetrical imaging properties of the capillary lens as described above thus the rear aperture angle $\beta$ is reduced in a similar manner. Therein, in the method of the present invention the focal depth $d_F$ of the XRF spectrometer is increased. Preferably the rear aperture angle $\beta$ of the polycapillary lens (preferably always) equals the front aperture angle $\alpha$ of the polycapillary lens.

According to a preferred embodiment, the method of the present invention further comprises the step of estimating a required target focal depth based on a topography of the target. Therein, the estimation might be based on a priori information, e.g. information on actual heights of structures, e.g. condensers, mounted to the target, e.g. a PCB, or information on a surface roughness of the target. Alternatively preferred, the method further comprises the step of measuring a topography of the target, e.g. by using an initial measurement of the XRF spectrometer or by using another tool, e.g. an electron microscope. In this preferred embodiment of the method of the invention, the focal depth $d_F$ of the XRF spectrometer is set based on the estimated or measured target topography. Preferably, the focal depth of the spectrometer is set by inserting a suitable pinhole into the primary X-ray radiation between an anode of the X-ray tube and a capillary lens of the spectrometer as described above.

According to a further preferred embodiment, the method of the invention further comprises the step of scanning the target in at least one of an X- and Y-direction, preferably also in Z-direction. Therein, line- or point-wise scanning of the target is preferably enabled via a movable target stage, X-ray source and/or X-ray optic that are controlled by a control unit configured for scanning of the target. In the method of the present invention in such a scanning measurement along the target preferably the focal depth $d_F$ of the XRF spectrometer is adapted while scanning the target. In other words, in a single scan process of the target the focal depth of the spectrometer is varied across the target. Therein, the variation of the focal depth of the spectrometer is preferably performed in dependence of topography data of the sample. In other words, a required target focal depth is preferably estimated for each point, each line or regions of a scanning scheme of a target and the focal depth of the XRF spectrometer is set based on the respective estimated or measured target topography for each of the points, lines or regions of the scanning scheme individually. Hence, a target is measured with the suitable focal depth at each position along the target.

Another aspect of the present invention relates to the use of an aperture system of the present invention for adjusting the focal depth of an X-ray fluorescence, XRF, spectrometer. Therein, the XRF spectrometer comprises an X-ray tube with an anode emitting a divergent X-ray beam and a capillary lens configured to focus the divergent X-ray beam onto a target.

According to the invention, an aperture system comprising at least one pinhole that is configured for reducing a beam cross section of the divergent X-ray beam, i.e. has a size that is adapted to the installation position of the aperture system, is used while being positioned between the anode of the X-ray tube and the polycapillary lens.

Another aspect of the present invention relates to a computer program that configures a data processing apparatus to perform a method for adjusting the focal depth of an XRF spectrometer as described above after being loaded into a memory element of the data processing apparatus. The data processing apparatus preferably is connected to an XRF spectrometer and/or to an aperture system as described above. Further preferred, the present invention relates to a computer readable memory element with a computer program as described above saved thereon, particularly with a computer program that allows a data processing apparatus to perform a method for adjusting the focal depth as described above after being loaded to a memory element of a data processing apparatus as described above.

The electronic or electric devices and/or any other relevant devices or components according to embodiments of the present invention described herein, except those described explicitly as hardware, may be implemented utilizing any suitable hardware, firmware (e.g. an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. The electrical connections or interconnections described herein may be realized by wires or conducting elements, e.g. on a PCB or another kind of circuit carrier. The conducting elements may comprise metallization, e.g. surface metallization and/or pins, and/or may comprise conductive polymers or ceramics. Further electrical energy might be transmitted via wireless connections, e.g. using electromagnetic radiation and/or light.

Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like.

Also, a person of skill in the art should recognize that the functionality of various computing devices may be combined or integrated into a single computing device, or the functionality of a particular computing device may be distributed across one or more other computing devices without departing from the scope of the exemplary embodiments of the present invention.

Further aspects and preferred embodiments of the present invention result from the dependent claims, the drawings and the following description of the drawings. Different disclosed embodiments are advantageously combined with each other if not stated otherwise.

BRIEF DESCRIPTION OF THE DRAWINGS

The features of the invention become apparent to those skilled in the art by the detailed description of exemplary embodiments with reference to the attached drawings. The patent or application file contains at least one drawing executed in color. Copies of this patent or patent application publication with color drawing(s) will be provided by the Office upon request and payment of the necessary fee.

DETAILED DESCRIPTION OF THE DRAWINGS

Figure 1:
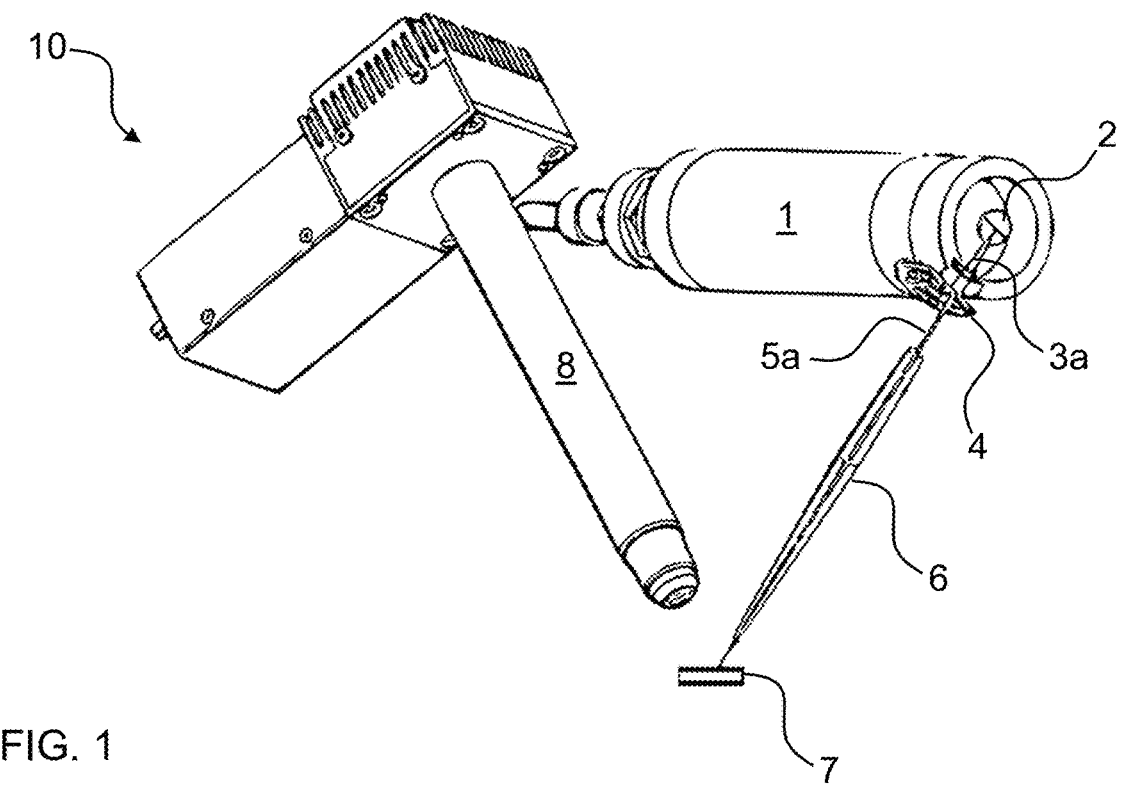
FIG. 1 shows a schematic illustration of a XRF spectrometer according to an embodiment.

Reference will now be made in detail to embodiments, examples of which are illustrated in the accompanying drawings. Effects and features of the exemplary embodiments, and implementation methods thereof will be described with reference to the accompanying drawings. In the drawings, like reference numerals denote like elements, and redundant descriptions are omitted. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art.

Accordingly, processes, elements, and techniques that are not considered necessary to those having ordinary skill in the art for a complete understanding of the aspects and features of the present invention may not be described.

As used herein, the term "and/or" includes any and all combinations of one or more of the associated listed items. Further, the use of "may" when describing embodiments of the present invention refers to "one or more embodiments of the present invention." In the following description of embodiments of the present invention, the terms of a singular form may include plural forms unless the context clearly indicates otherwise.

It will be understood that although the terms "first" and "second" are used to describe various elements, these elements should not be limited by these terms. These terms are only used to distinguish one element from another element. For example, a first element may be named a second element and, similarly, a second element may be named a first element, without departing from the scope of the present invention. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent deviations in measured or calculated values that would be recognized by those of ordinary skill in the art. Further, if the term "substantially" is used in combination with a feature that could be expressed using a numeric value, the term "substantially" denotes a range of +/−5% of the value centered on the value.

Figure 2:
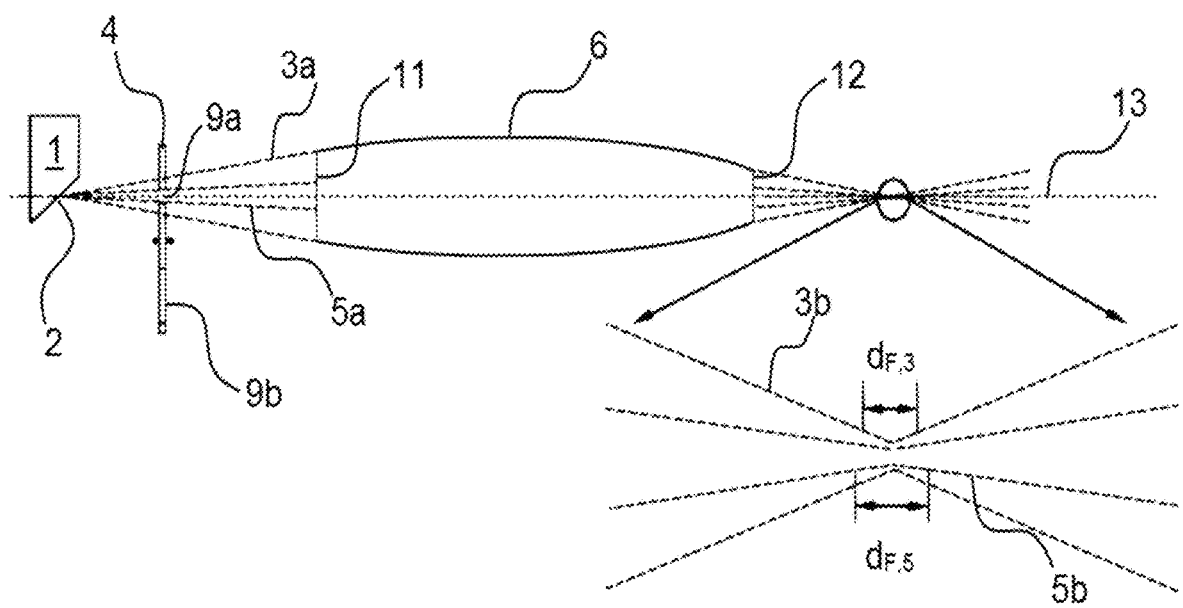
FIG. 2 shows a schematic cross sectional illustration of a beam path in an XRF spectrometer according to an embodiment.
Figure 3:
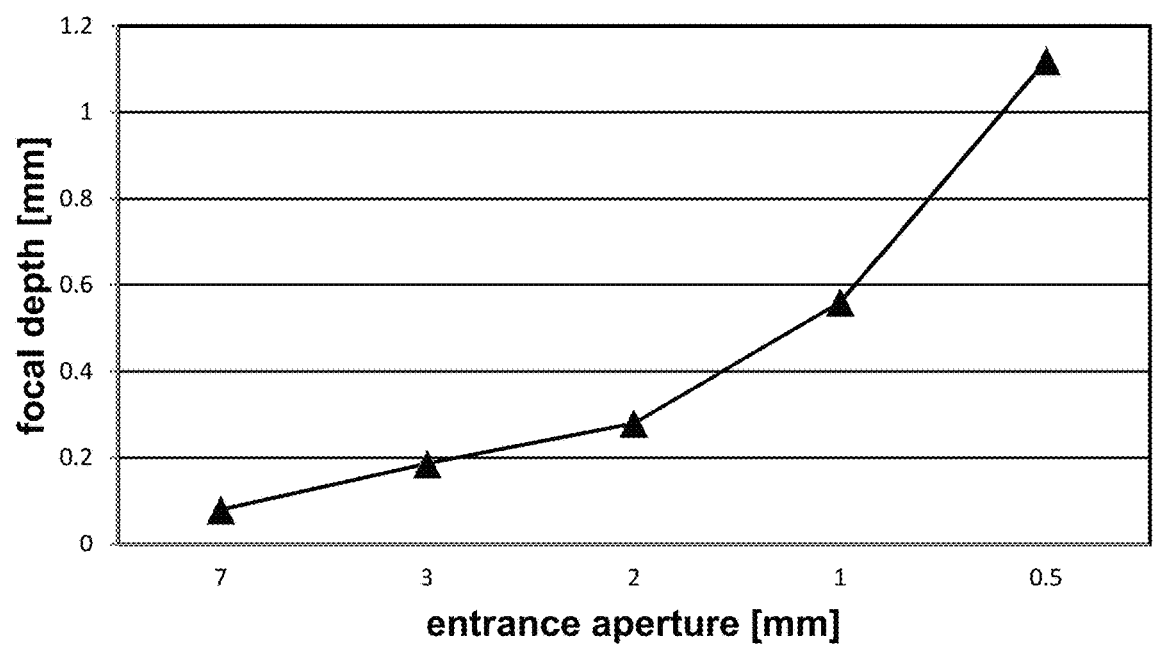
FIG. 3 shows the relation between a variation of entrance aperture of a capillary lens in the claimed method and the impact on focal depth of an XRF spectrometer.

FIGS. 1 and 2 shows a schematic illustration of a micro XRF spectrometer 10 according to an embodiment and of a cross sectional schematic illustration of an X-ray beam path therein.

The XRF spectrometer 10 comprises a microfocus X-ray tube 1 with an anode 2 that emits a divergent primary X-ray beam 3a. Outer parts of the divergent primary X-ray beam 3a are blocked outside of the X-ray tube 1 by an aperture system in the form of a revolver 4 comprising a plurality of pinholes 9a, 9b with varying sizes. Therein, the primary X-ray beam 3a is transferred to a divergent X-ray beam with reduced beam cross section 5a. This reduced beam cross section 5a is equal to or smaller than the entrance aperture 11 of a subsequent polycapillary lens 6. A focal point of the microfocus X-ray tube 1 at the anode 2 is positioned in the front focal point of the polycapillary lens 6.

The polycapillary lens 6 focuses the divergent X-ray beam with reduced cross section 5a onto a target 7 that can be moved in X-, Y-, and Z-direction by a movable sample stage (not shown) of the spectrometer 10. Therein, the movable sample stage preferably comprises micro-actuators. Alternatively, a functional unit comprising the X-ray source 1, the aperture unit 4 and the polycapillary lens 6 is movable at least in an X- and Y-direction, preferably also in Z-direction. Therein, the functional unit can be pivoted via a goniometer, at least with respect to the X- and Y-direction. By providing at least one of such pivotable and/or movable functional unit and such movable target point-wise scanning of the system is enabled.

X-ray fluorescence radiation emitted by the sample 7 in response to the incident X-rays and parts of the incident convergent X-ray beam with reduced cross section 5b that have been scattered or diffracted by the sample 7 are then measured by detector 8 that transfers the corresponding detector signals to a suitable electronic evaluation unit (not shown). By combining the movement of the sample 7 and the detection of radiation emitted by the sample 7, various properties of the sample 7 are determined in an imaging and/or spectrometric method with spectrometer 10.

As can be seen in the cross sectional schematic beam path of FIG. 2 within the spectrometer 10 of the invention, by inserting the specific pinhole 9a of the plurality of pinholes 9a, 9b of the revolver 4 into the primary divergent X-ray beam 3a it is reduced to a divergent X-ray beam with reduced cross section 5a illuminating only a reduced area of the entrance aperture 11 of the polycapillary lens 6. Thus, the front aperture angle α enclosed between the optical axis 13 and an outermost ray of the divergent X-ray beam with reduced beam cross section 5a is decreased as well. Similarly, only a reduced area of the exit aperture 12 of the polycapillary lens 6 emits (transmits) X-ray beams such that by positioning pinhole 9A in primary divergent X-ray beam 3a also a cross section of a convergent primary X-ray beam 3b exiting the polycapillary lens 6 is reduced to a convergent X-ray beam 5b.

A rear focal point of polycapillary lens 6 is shown in FIG. 2 in a magnified detailed illustration. Therein, two focal lengths $d_F$ are indicated that each correspond to a range around the rear focal point in which the focal width of the respective X-ray beam doubled with respect to the smallest focal width of the respective X-ray beam at the rear focal point. As illustrated in FIG. 2, a focal length $d_{F3}$ of the primary convergent X-ray beam 3b is smaller than a focal length $d_{F5}$ of the convergent X-ray beam with reduced beam cross section 5b. Inserting pinhole 9a into the primary divergent X-ray beam 3a thus increased the focal depth.

Table 1 below shows computed values for a simulation based on a beam path as shown in FIG. 2. Therein, a front focal length between the entrance aperture 11 of the polycapillary lens 6 and the anode 2 of the X-ray tube 1 is fixed to 50 mm and a rear focal length between the exit aperture 12 of the polycapillary lens 6 is fixed to 10 mm. Different from the illustration in FIG. 2, the minimal focal width at the rear focal point equals 20 µm independently of the shown aperture. In this regard, the illustration of FIG. 2 is a mere illustrative example.

As shown in Table 1, the focal depth has been defined as the length of a range around the rear focal point in which the focal width doubles (2×FWHM). The computation underlying the numbers of Table 1 was conducted based on the assumption that the exit aperture 12 of the polycapillary lens 6 changes by the same ratio as the entrance aperture 11. The columns of Table 1 show the numbers for the entrance aperture without a pinhole being inserted in divergent primary X-ray beam 3a and with pinholes of various sizes 9a, 9b inserted therein. In Table 1 the pinholes are indicated by the size to which they reduce the entrance aperture 11.

As can be conducted from the numbers of Table 1, without a pinhole in the X-ray beam 3a the entrance aperture 11 of the polycapillary lens 6 equals 7 mm, which is equal to the diameter of the polycapillary lens 6. By inserting different pinholes 9a, 9b into the primary X-ray beam 3a for reducing the beam cross section, the entrance aperture 11 decreases to 3 mm, 2 mm, 1 mm and 0.5 mm, respectively. From the numbers shown in Table 1 it can be seen that the length of the focal depth increased by the same factor as the entrance aperture 11 has been decreased by reducing the cross section of X-ray beam 5a by the pinholes 9a, 9b of revolver 4.

TABLE 1

| parameters polycapillary lens | | without pinhole | Pinholes | | | |
|---|---|---|---|---|---|---|
| | | | 3 | 2 | 1 | 0.5 |
| front focal length | mm | 50 | 50 | 50 | 50 | 50 |
| entrance aperture | mm | 7 | 3 | 2 | 1 | 0.5 |
| rear focal length | mm | 10 | 10 | 10 | 10 | 10 |
| exit aperture | mm | 2.5 | 1.071 | 0.714 | 0.357 | 0.179 |
| rear focal spot size | µm | 20 | 20 | 20 | 20 | 20 |
| front aperture angle | degree | 8.01 | 3.44 | 2.29 | 1.15 | 0.57 |
| rear aperture angle | degree | 14.25 | 6.13 | 4.09 | 2.05 | 1.02 |
| focal depth (2 × FWHM) | mm | 0.080 | 0.187 | 0.280 | 0.560 | 1.120 |

Figure 4:
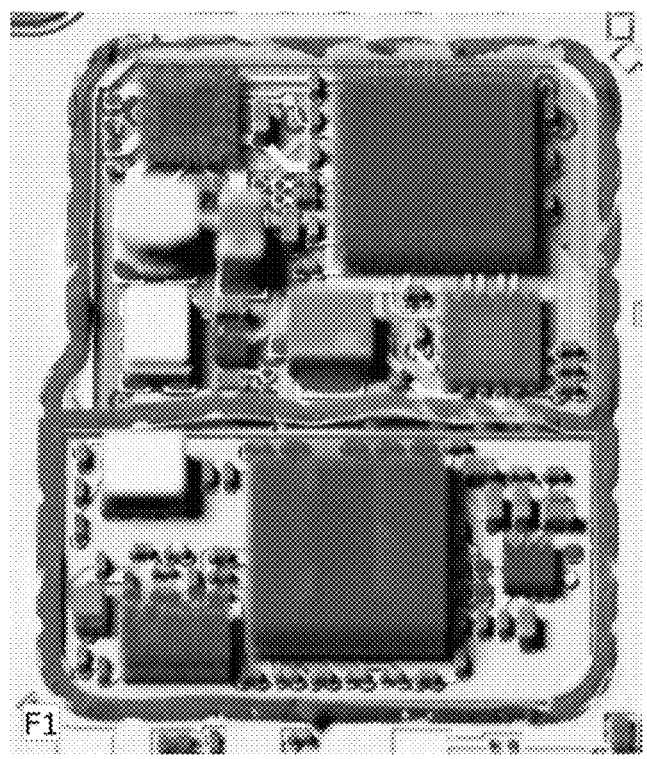
FIG. 4 shows a picture of various microelectronic devices that are surface mounted to a printed circuit board, PCB, obtained (A) with a XRF spectrometer according to the prior art and (B) with a XRF spectrometer according to the present invention.
Figure 4:
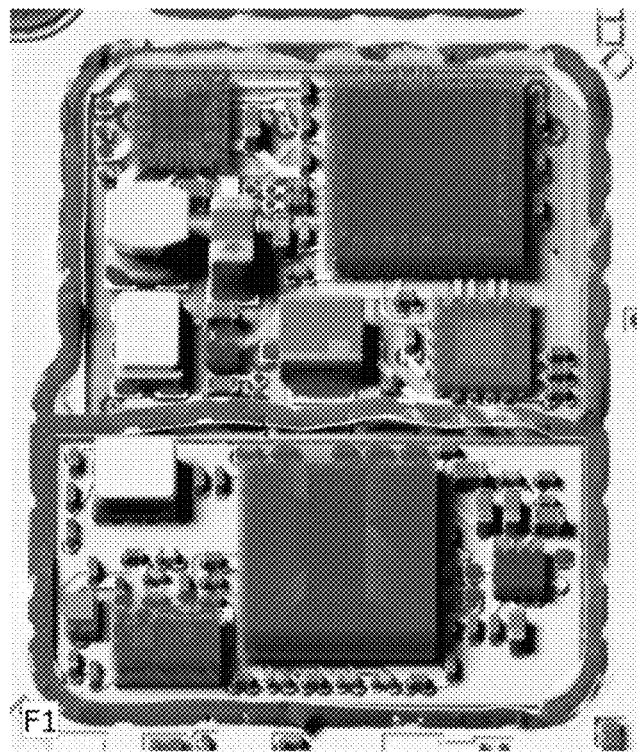

FIG. 4 shows two pictures of a printed circuit board, PCB, with various microelectronic devices surface mounted thereto. Both of these pictures have been obtained with the "M4 TORNADO" Micro-XRF spectrometer of Bruker Nano. This Micro-XRF spectrometer is particularly designed for XRF measurements of flat samples such as printed circuit boards.

The picture of FIG. 4 (A) was obtained with this spectrometer in standard configuration, i.e. with a full entry aperture of the capillary lens being illuminated by the primary X-ray radiation. On the contrary, the picture of FIG. 4 (B) was obtained with a spectrometer equipped with an aperture device according to an embodiment of the present invention, wherein the entry aperture of the capillary lens was reduced to 1 mm by a pinhole introduced into the primary divergent X-ray radiation between the anode of the X-ray tube and the capillary lens.

In both of the pictures of FIGS. 4 (A), (B) the focus point of the incident X-ray excitation radiation was set to the level of the PCB. In the picture obtained with the standard setup of the tool as shown in FIG. 4 (A), the images of the microelectronic devices surface mounted to the PCB quickly blur out with increasing distance from the PCB. Exemplarily, the wiring between the microelectronic devices and the PCB cannot be easily recognized. However in the image of FIG. 4 (B) obtained with the setup according to the invention, the focal depth $d_F$ is significantly increased such that almost all of the microelectronic devices are imaged sharply from their bottoms mounted to the PCB to their tops. Further, the wiring, e.g. connecting the microelectronic device shown in the upper right corner and the PCB, can be clearly recognized in the picture of FIG. 4 (B). Thus, the improvement obtained by applying the aperture system of the present invention is clearly visible in FIGS. 4 (A) and (B).

Figure 5:
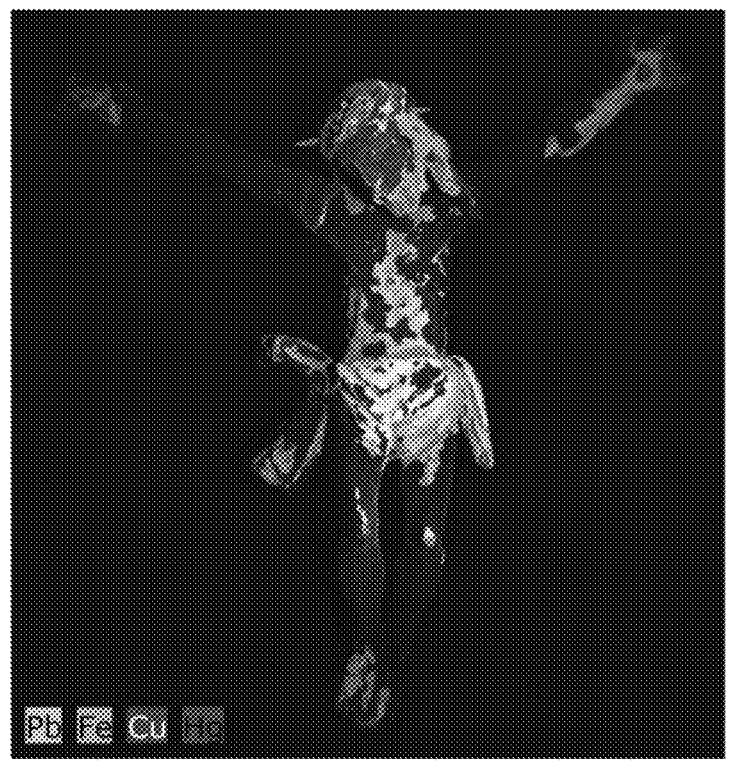
FIG. 5 shows pictures of a 3-dimensional object obtained with an XRF spectrometer, particularly (A) a total of the 3D object, (B) a detail of the 3D object with standard focal depth and (C) the same detail of the 3D object with a focal depth that has been adapted according to the method of the invention.
Figure 5:
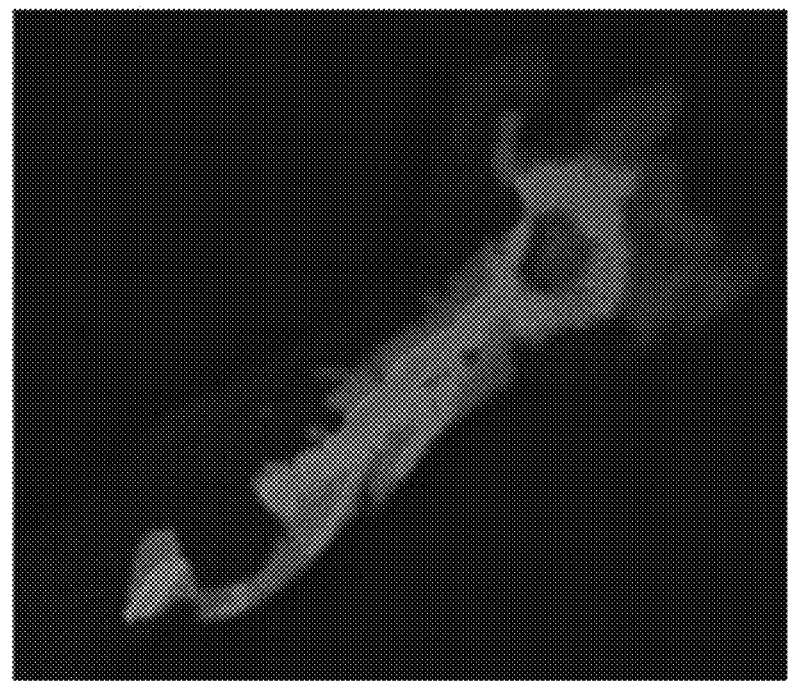
Figure 5:
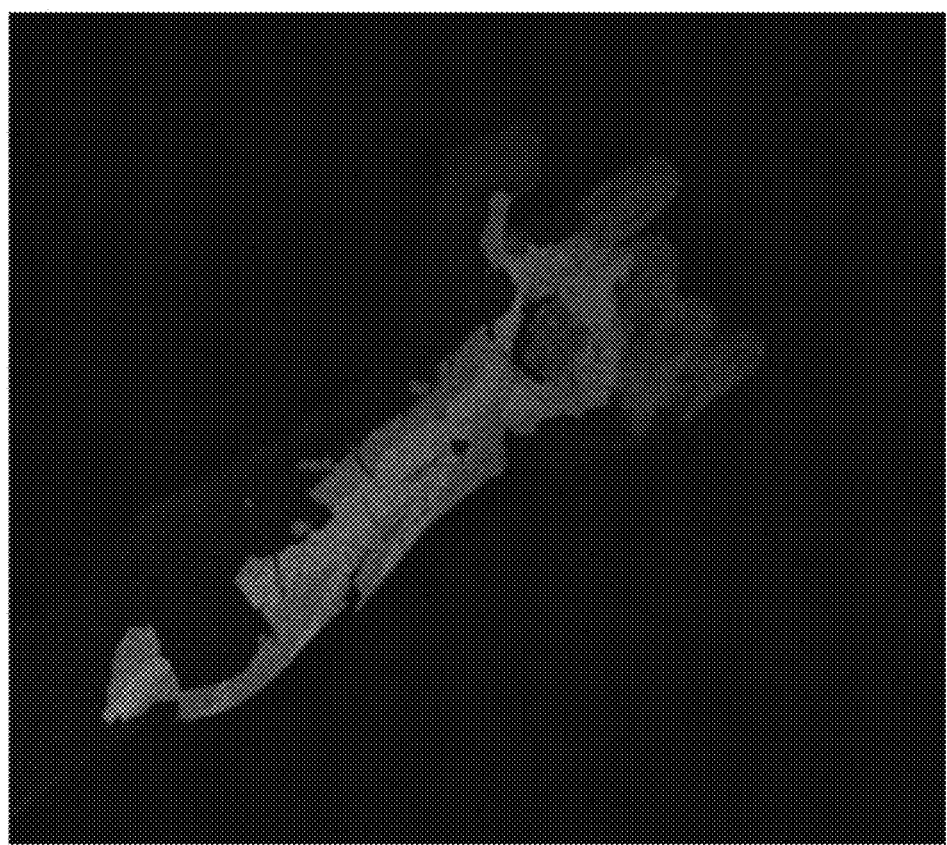

FIG. 5 shows pictures of a 3-dimensional object, particularly of a painted wooden crucifix with a height of approximately 150 mm that has been obtained with an "M6 Jetstream" large area micro X-ray fluorescence spectrometer of Bruker Nano. This Micro-XRF spectrometer is particularly designed for an on-destructive elemental analysis of large sample and comprises a measurement rig that can be tilted for allowing samples to be scanned either horizontally or vertically via a movable scanning head comprising an X-ray source tube and a capillary optic.

The total of the crucifix as shown in FIG. 5 (A) as well as the detail of the crucifix as shown in FIG. 5 (B) have been obtained with this spectrometer in standard configuration, i.e. with a full entry aperture of the capillary lens being illuminated by the primary X-ray radiation. On the contrary, the same detail of the crucifix as shown in FIG. 5 (C) was obtained with a spectrometer equipped with an aperture device according to an embodiment of the present invention. Therein, a pinhole with a diameter of 500 µm has been introduced into the primary divergent X-ray radiation between the anode of the X-ray tube and the capillary lens.

As illustrated in FIG. 5 (A), four different elements, namely lead, iron, copper and mercury are distinguished within a painting of the crucifix. X-ray fluorescence emitted by the detail shown in FIG. 5 (B) has been analyzed for 12 h without an additional pinhole within the primary X-ray radiation. However, due to the three-dimensional shape of the figurine's right arm, it cannot be proper focused and hence the distribution of copper and mercury is resolved with lower detail. The picture of FIG. 5 (C) has been obtained by detecting X-ray fluorescence of the figurine for 72 h with an additional pinhole of 500 µm diameter inserted in the primary X-ray radiation between the anode of the X-ray tube and polycapillary lens. As it can be seen in FIG. 5 (B), the focal depth of the recording is significantly increased and hence the distribution of the elements copper and mercury is resolved in more detail. Hence, the advantages obtained by the spectrometer, the aperture system and the method of the present invention can be clearly obtained from the FIGS. 5 (A), (B) and (C).

REFERENCE SIGNS

1 X-ray tube
2 anode (of X-ray tube)
3a divergent primary X-ray beam
3b convergent primary X-ray beam
4 aperture system
5a divergent X-ray beam with reduced beam cross section
5b convergent X-ray beam with reduced beam cross section
6 capillary lens
7 target
8 detector
9a; 9b pinholes
10 XRF spectrometer
11 entrance aperture
12 exit aperture
13 optical axis
$d_{F3}$, $d_{F3}$ focal length

The invention claimed is:

1. An X-ray fluorescence, XRF spectrometer, for measuring X-ray fluorescence emitted by a target, the XRF spectrometer comprising:
 an X-ray tube with an anode to emit a divergent X-ray beam;
 a capillary lens configured to focus the divergent X-ray beam on the target;
 an aperture system positioned between the anode of the X-ray tube and the capillary lens and comprising at least one pinhole; and
 a detector configured for detecting X-ray fluorescence radiation emitted by the target,
 wherein the at least one pinhole is configured for being inserted into the divergent X-ray beam and for reducing a beam cross section of the divergent X-ray beam between the anode and the capillary lens; and
 the XRF spectrometer further comprising a control unit configured for adapting the focal depth $d_F$ of the XRF spectrometer by controlling the beam cross section of the divergent X-ray beam via the aperture system and based on a topography of the target and/or while scanning the target in at least one selected from among X- and Y-directions.

2. The XRF spectrometer of claim 1, wherein a front focal point of the capillary lens is placed at the anode.

3. The XRF spectrometer of claim 1, wherein the X-ray tube is a microfocus tube and/or wherein the XRF spectrometer is a micro XRF spectrometer.

4. The XRF spectrometer of claim 1,
wherein the capillary lens has an entrance aperture, a front focal length, and a front aperture angle α that obey the equation:

$$\tan\alpha = \frac{\text{entrance aperture (11)}}{\text{front focal length}},$$

and wherein the front focal length corresponds to a distance between the entrance aperture and the anode, and/or
wherein the capillary lens has an exit aperture, a rear focal length, and a rear aperture angle β that obey the equation:

$$\tan\beta = \frac{\text{exit aperture (12)}}{\text{rear focal length}},$$

and wherein the rear focal length corresponds to the distance between the exit aperture and the target.

5. The XRF spectrometer of claim 1, wherein the aperture system comprises at least one pinhole of adjustable size.

6. The XRF spectrometer of claim 1, wherein the aperture system comprises a revolver or a slider, each with a plurality of pinholes of different sizes that are each configured for being individually inserted into the divergent X-ray beam.

7. The XRF spectrometer of claim 6, wherein the revolver or the slider further comprises at least one filter for spectrally modifying the divergent X-ray beam.

8. The XRF spectrometer of claim 6, further comprising an additional revolver or slider with at least one filter for spectrally modifying the divergent X-ray beam.

9. A method for adjusting the focal depth $d_F$ of an X-ray fluorescence, XRF, spectrometer comprising an X-ray tube with an anode to emit a divergent X-ray beam, a capillary lens configured to focus the divergent X-ray beam on a target, an aperture system positioned between the anode of the X-ray tube and the capillary lens and comprising at least one pinhole, and a control unit configured for controlling the aperture system and for performing the steps of:
 inserting one of the at least one pinhole in the divergent X-ray beam between the anode and the capillary lens;
 reducing a cross section of the divergent X-ray beam and a front aperture angle α of the capillary lens with one of the at least one pinhole;
 increasing the focal depth $d_F$ of the XRF spectrometer;
 estimating a required target focal depth based on a topography of the target; and
 setting the focal depth $d_F$ of the XRF spectrometer based on the estimated target focal depth.

10. A method for adjusting the focal depth $d_F$ of an X-ray fluorescence, XRF, spectrometer comprising an X-ray tube with an anode to emit a divergent X-ray beam, a capillary lens configured to focus the divergent X-ray beam on a target, an aperture system positioned between the anode of the X-ray tube and the capillary lens and comprising at least one pinhole, and a control unit configured for controlling the aperture system and for performing the steps of:
 inserting one of the at least one pinhole in the divergent X-ray beam between the anode and the capillary lens;
 reducing a cross section of the divergent X-ray beam and a front aperture angle α of the capillary lens with one of the at least one pinhole;
 increasing the focal depth $d_F$ of the XRF spectrometer;
 scanning the target in at least one selected from among X- and Y-directions; and
 adapting the focal depth $d_F$ of the XRF spectrometer while scanning the target.

* * * * *